US008735477B2

(12) United States Patent
Hill et al.

(10) Patent No.: US 8,735,477 B2
(45) Date of Patent: May 27, 2014

(54) METHOD FOR PRODUCING DIALKYLPHOSPHINIC ACIDS AND ESTERS AND SALTS THEREOF BY MEANS OF ACRYLNITRILES AND USE THEREOF

(75) Inventors: Michael Hill, Cologne (DE); Werner Krause, Huerth (DE); Martin Sicken, Cologne (DE)

(73) Assignee: Clariant Finance (BVI) Limited, Tortola (VG)

(*) Notice: Subject to any disclaimer, the term of this patent is extended or adjusted under 35 U.S.C. 154(b) by 263 days.

(21) Appl. No.: 13/127,069

(22) PCT Filed: Oct. 6, 2009

(86) PCT No.: PCT/EP2009/007131
§ 371 (c)(1),
(2), (4) Date: May 2, 2011

(87) PCT Pub. No.: WO2010/051891
PCT Pub. Date: May 14, 2010

(65) Prior Publication Data
US 2011/0213060 A1 Sep. 1, 2011

(30) Foreign Application Priority Data
Nov. 7, 2008 (DE) .......................... 10 2008 056 342

(51) Int. Cl.
*C08K 5/5313* (2006.01)
(52) U.S. Cl.
USPC ........... 524/133; 558/129; 558/137; 558/179; 560/129; 562/24
(58) Field of Classification Search
USPC ....................................................... 524/133
See application file for complete search history.

(56) References Cited

U.S. PATENT DOCUMENTS

| | | | |
|---|---|---|---|
| 3,345,432 A | 10/1967 | Gillham et al. |
| 3,784,638 A | 1/1974 | Lambert |
| 3,875,263 A | 4/1975 | Herwig et al. |
| 3,939,050 A | 2/1976 | Kleiner et al. |
| 3,941,752 A | 3/1976 | Kleiner et al. |
| 3,962,194 A | 6/1976 | Bollert et al. |
| 4,001,352 A | 1/1977 | Kleiner et al. |
| 4,035,343 A | 7/1977 | Bollert et al. |
| 4,069,245 A | 1/1978 | Dursch et al. |
| 4,069,247 A | 1/1978 | Kleiner |
| 4,079,049 A | 3/1978 | Ramsey et al. |
| 4,168,267 A | 9/1979 | Petrillo |
| 4,235,991 A | 11/1980 | Digiacomo |
| 4,337,201 A | 6/1982 | Petrillo |
| 4,374,131 A | 2/1983 | Petrillo |
| 4,381,297 A | 4/1983 | Karanewsky et al. |
| 4,427,665 A | 1/1984 | Karanewsky et al. |
| 4,555,506 A | 11/1985 | Karanewsky et al. |
| 4,594,199 A | 6/1986 | Thottathil et al. |
| 4,602,092 A | 7/1986 | Thottathil et al. |
| 4,634,689 A | 1/1987 | Witkowski et al. |
| 5,013,863 A | 5/1991 | Baylis et al. |
| 5,153,347 A | 10/1992 | Lloyd |
| 5,190,934 A | 3/1993 | Mickel et al. |
| 5,229,379 A | 7/1993 | Marescaux et al. |
| 5,391,743 A | 2/1995 | Ebitino et al. |
| 5,407,922 A | 4/1995 | Marescaux et al. |
| 5,545,631 A | 8/1996 | Marescaux |
| 5,739,123 A | 4/1998 | Norcini et al. |
| 5,780,534 A | 7/1998 | Kleiner et al. |

(Continued)

FOREIGN PATENT DOCUMENTS

| | | |
|---|---|---|
| AT | 243952 | 12/1965 |
| DE | 1494922 | 6/1969 |

(Continued)

OTHER PUBLICATIONS

US 6,248,921, 06/2001, Weferling et al. (withdrawn).
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obschchei Khimii), 74(6) pp. 864-872; XP002561442 (2004).
PCT International Search Report for PCT/EP2009/007123, mailed Jan. 29, 2010.

(Continued)

*Primary Examiner* — Doris Lee
(74) *Attorney, Agent, or Firm* — Anthony A. Bisulca

(57) ABSTRACT

The invention relates to a method for producing mono-carboxyfunctionalized dialkylphosphinic acids and esters and salts thereof, characterized in that a) a phosphinic acid source (I) is reacted with olefins (IV) to yield an alkylphosphonic acid, salt or ester (II) thereof in the presence of a catalyst A, b) the thus obtained alkylphosphonic acid, salt or ester (II) thereof is reacted with compounds of formula (V) to yield mono-functionalized dialkylphosphinic acid derivatives (VI) in the presence of a catalyst B, and c) the thus obtained mono-functionalized dialkylphosphinic acid derivatives (VI) are reacted to yield a mono-carboxyfunctionalized diakylphosphinic acid derivative (III) in the presence of a catalyst C, wherein $R^1$, $R^2$, $R^3$, $R^4$, $R^5$, $R^6$, $R^7$ are the same or different and stand independently of each other, among other things, for H, $C_1$-$C_{18}$ alkyl, $C_6$-$C_{18}$ aryl, $C_6$-$C_{18}$ aralkyl, $C_6$-$C_{18}$ alkylaryl and X and Y are the same or different and stand independently of each for H, $C_1$-$C_{18}$ alkyl, $C_6$-$C_{18}$ aryl, $C_6$-$C_{18}$ aralkyl, $C_6$-$C_{18}$ alkylaryl, Mg, Ca, Al, Sb, Sn, Ge, Ti, Fe, Zr, Zn, Ce, Bi, Sr, Mn, Cu, Ni, Li, Na, K and/or a protonized nitrogen base, and the catalyst A is formed by transition metals and/or transition metal compounds and/or catalyst systems composed of a transition metal and/or a transition metal compound and at least one ligand, and catalyst B is formed by compounds forming peroxides and/or peroxo compounds and/or azo compounds and/or alkali metals and/or alkaline earth metals, alkali hydrides, alkaline earth hydrides and/or alkali alcoholates and alkaline earth alcoholates, and catalyst C is an acid or a base.

12 Claims, No Drawings

(56) References Cited

U.S. PATENT DOCUMENTS

| | | | |
|---|---|---|---|
| 6,013,707 A | 1/2000 | Kleiner et al. | |
| 6,090,968 A | 7/2000 | Horold et al. | |
| 6,214,812 B1 | 4/2001 | Karpeisky | |
| 6,355,832 B1 | 3/2002 | Weferling et al. | |
| 6,384,022 B1 | 5/2002 | Jackson et al. | |
| 6,569,974 B1 | 5/2003 | Sicken et al. | |
| 6,727,335 B2 | 4/2004 | Sicken et al. | |
| 6,855,757 B2 | 2/2005 | Horold et al. | |
| 7,446,140 B2 | 11/2008 | Bauer | |
| 7,473,794 B2 | 1/2009 | Wehner et al. | |
| 7,485,745 B2 | 2/2009 | Maas et al. | |
| 7,749,985 B2 | 7/2010 | Gallop et al. | |
| 7,829,736 B2 | 11/2010 | Wehner et al. | |
| 8,084,518 B2 | 12/2011 | Bauer | |
| 8,097,753 B2 | 1/2012 | Maas et al. | |
| 2002/0187977 A1 | 12/2002 | Pearlman et al. | |
| 2003/0171466 A1 | 9/2003 | Horold et al. | |
| 2003/0216533 A1 | 11/2003 | Sicken et al. | |
| 2005/0187196 A1 | 8/2005 | Madrid et al. | |
| 2006/0084734 A1 | 4/2006 | Bauer et al. | |
| 2006/0194973 A1 | 8/2006 | Gainer et al. | |
| 2006/0264654 A1 | 11/2006 | Wehner et al. | |
| 2007/0210288 A1* | 9/2007 | Maas et al. | 252/601 |
| 2007/0213436 A1 | 9/2007 | Maas et al. | |
| 2007/0213563 A1 | 9/2007 | Maas et al. | |
| 2008/0183009 A1 | 7/2008 | Wehner et al. | |
| 2008/0214708 A1 | 9/2008 | Bauer et al. | |
| 2009/0286759 A1 | 11/2009 | Gallop et al. | |
| 2010/0093239 A1 | 4/2010 | Bauer et al. | |
| 2011/0201732 A1 | 8/2011 | Hill et al. | |
| 2011/0201733 A1 | 8/2011 | Hill et al. | |
| 2011/0213052 A1 | 9/2011 | Hill et al. | |
| 2011/0213059 A1 | 9/2011 | Hill et al. | |
| 2011/0213061 A1 | 9/2011 | Hill et al. | |
| 2011/0213062 A1 | 9/2011 | Hill et al. | |
| 2011/0213078 A1 | 9/2011 | Hill et al. | |
| 2011/0213079 A1 | 9/2011 | Hill et al. | |
| 2011/0213080 A1 | 9/2011 | Hill et al. | |
| 2011/0224339 A1 | 9/2011 | Hill et al. | |
| 2011/0224340 A1 | 9/2011 | Hill et al. | |
| 2011/0237720 A1 | 9/2011 | Hill et al. | |
| 2011/0237721 A1 | 9/2011 | Hill et al. | |
| 2011/0237722 A1 | 9/2011 | Hill et al. | |
| 2011/0245385 A1 | 10/2011 | Hill et al. | |
| 2011/0245386 A1 | 10/2011 | Hill et al. | |
| 2011/0251310 A1 | 10/2011 | Hill et al. | |
| 2011/0251312 A1 | 10/2011 | Hill et al. | |
| 2011/0251314 A1 | 10/2011 | Hill et al. | |
| 2011/0251315 A1 | 10/2011 | Hill et al. | |
| 2011/0275744 A1 | 11/2011 | Hill et al. | |
| 2011/0281983 A1 | 11/2011 | Hill et al. | |
| 2012/0064790 A1 | 3/2012 | Bauer et al. | |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

English Translation of the PCT International Preliminary Report on Patentability PCT/EP2009/007123 mailed May 19, 2011.

Montchamp; "Recent advances in phosphorus-carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).

Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).

Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).

Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).

Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).

Courdray L. et al.: "Allylic Phosphinates via Pd-Catalyzed Allylation of H-Phosphinic Acids with Allylic Alcohols;" Organic letters, vol. 10, No. 6, pp. 1123-1126 XP002561368 (Feb. 21, 2008).

Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).

Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).

Houben-Weyl, vol. 1211, pp. 258-259 (Apr. 22, 1963).

Houben-Weyl, vol. 1211, p. 306 (Apr. 22, 1963).

English abstract of Khairullin et al,"Reaction of chlorides of acids of trivalent phosphorous with conjugated systems I. Reaction of ethylphosphonous dichloride with alpha-beta-unsaturated acids" Zh. Obshch. Khimii. 36, pp. 289-296 (1996).

PCT International search report for PCT/EP2009/007124, mailed Feb. 22, 2010.

PCT International Preliminary Report on Patentability for PCT/EP2009/007124, mailed May 19, 2011.

Piotr Majewski: "A New Method for the Preparation of Bis(1-hydroxyalkyl)-phosphinic Acids;" Synthesis, vol. 6, pp. 555-557, XP002558292 (1987).

Hung Kuei Lin et al.: "Competitive inhibition of interfacial catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).

Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP002558647 (1989).

(56) References Cited

OTHER PUBLICATIONS

PCT International Search Report for PCT/EP2009/007125, mailed Feb. 22, 2010.
English translation of PCT International Preliminary Report on Patentability for PCT/EP2009/007125, mailed May 19, 2011.
PCT International search report for PCT/EP2009/007126, mailed Sep. 2, 2010.
English translation of PCT International Preliminary Report on Patentability for PCT/EP2009/007126, mailed May 19, 2011.
Froestl W. et al.: "Phosphinic Acid Analogues of Gaba. 2. Selective, Orally Acitive Gabab Antagonists," Journal of Medicinal Chemistry, American Chemical Society, Washington, US, vol. 38, No. 17, pp. 3313-3331, XP000999491 (Jan. 1, 1995).
PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975.
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorous-containing Aminocarboxylic: XIV. Synthesis of Analogs of [alpha]—Substituted Glutamic Acid" Russian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Gareev et al.: "Stereochemistry of a 1,3-dipolar cycloaddition of diazomethane to alpha-substituted vinylphosphoryl compounds containing a chiral phosphorous atom" XP002567581 (1979).
Chemical Abstracts Service, Columbus, Ohio, US: Raevskii et al. "Electron-donor and acceptro functions of physiology active and model compounds. V. Calculation of the electron-donor function of phosphoryl oxygen" XP002567582 (1984).
Isabelle Abrunhosa Thomas et al.: "Alkylation of H-Phosphinate Esters under Basic Conditions;" Journal of Organic Chemistry, American Chemical Society, Easton,; US vol. 472, No. 8 pp. 2851-2856 XP002530192 (Jan. 1, 2007).
Catherine Ruflin et al.: "Tetrakis(trimethylsilyl)hypophosphate P2O2(OTMS)4: Synthesis, reactivity and application as flame retardant;" Heteroatom Chemistry, VCH publishers, Defield Beach, FL, US, vol. 18, No. 7 pp. 721-731 XP009118331 (Nov. 6, 2007).
PCT International Search Report for PCT/EP2009/007131, mailed Feb. 8, 2010.
English translation of the PCT International Preliminary Report on Patentability for PCT/EP2009/007131, mailed May 19, 2011.
PCT International Preliminary Report on Patentability for PCT/EP2009/007132, mailed Feb. 15, 2010.
English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.

Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Dienes, and Allylic Electrophiles: Methodology for the Synthesis of Allylic H-Phosphinates" J. Org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a Building Block for Phosphinyl Peptides" Synlett, No. 9, pp. 1471-1474, XP 002567142 (Jan. 1, 2002).
PCT International Search Report for PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).
Pudovick et al.: "Free Radical Reaction of Addition of Partial Esters of Phosphorus Acids to Acetylenic Hydrocarbons;" J. Gen. Chem. USSR, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).
Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.

(56) References Cited

OTHER PUBLICATIONS

Sasse K ED—Sasse K: "Houben-Weyl Methoden der Organischen Chemie", Organische Phosphor-Verbindungen; [Methoden der Organischen Chemie], Stuttgart, G. Thieme Verlag DE, XP002500739, pp. 257-259, 261, 294-301 (Jan. 1, 1963).

"1" In: Sasse K Ed—Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).

Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).

Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).

Anderson et al.: "Antidiabetic agents: a new class of reversible carnitine palmitoyltrasferase I inhibitors;" J. Med. Chem., vol. 38, No. 18, pp. 3448-3450 XP002564326 (1995).

Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).

Issleib, et al.: "Synthese und Reaktionsverhalten der Athylen-bis-organophosphine;" Chemische Berichte, vol. 101, pp. 2197-2202 XP009126251.

PCT International Search Report for PCT/EP2009/007143, mailed Feb. 17, 2010.

English translation of the PCT International Preliminary Report on Patentability for PCT/EP2009/007143, mailed Jun. 30, 2011.

Regitz: "Houben-Weyl Methoden der Organishcen Chemie" p. 188, (Jan. 1, 1982).

Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).

Database Beilstein [online] Beilstein Institute for Organic Chemistry, Frankfurt-Main, DE; Database accession No. Reaction ID 938840 XP002557780 (1962).

Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).

Sasse K ED—Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).

Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).

Maier: "Organic Phosphorus compounds 91.1 Synthesis and Properties of 1-Amino-2-Arylethylphosphinic and -Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).

\* cited by examiner

METHOD FOR PRODUCING DIALKYLPHOSPHINIC ACIDS AND ESTERS AND SALTS THEREOF BY MEANS OF ACRYLNITRILES AND USE THEREOF

This invention relates to a method for producing dialkylphosphinic acids, esters and salts by means of acrylonitriles and also to their use.

There are certain dialkylphosphinic acids, known as monocarboxy-functionalized dialkylphosphinic acids, as hereinbelow defined, of which hitherto very substantially only the esters are available. The latter are obtainable via multiple steps proceeding from phosphonous dihalides. These include reaction of dihalophosphines with activated olefinic compounds such as acrylic acid followed by the esterification with alcohols of the acid chloride and anhydride derivatives initially formed (V. K. Khairullin, R. R. Shagidullin, Zh. Obshch. Khim. 36, 289-296).

Dialkylphosphinic acids for the purposes of the present invention are thus always monocarboxy-functionalized dialkylphosphinic acids even where this is not expressly mentioned. This definition includes the corresponding esters and salts.

Such dialkylphosphinic esters are also obtained on adding phosphonous esters onto α,β-unsaturated carboxylic esters in the presence of peroxidic catalysts (Houben-Weyl, volume 1211, pages 258-259). The phosphonous esters themselves are prepared from phosphonous dihalides by reaction with alcohols, or hydrolysis, and subsequent esterification. The aforementioned phosphonous dihalides themselves are prepared in a costly and inconvenient synthesis from phosphoryl trichloride and alkyl chloride in the presence of aluminum chloride (Houben-Weyl, volume 1211, page 306). The reaction is strongly exothermic and difficult to control on an industrial scale. In addition, the reaction by-produces various products which, like some of the aforementioned starting materials also, are toxic and/or corrosive, i.e., extremely undesirable (particularly since the products are not obtainable free of halogen).

A further method for producing monocarboxy-functionalized dialkylphosphinic esters is based on the reaction of yellow phosphorus with methyl chloride to form methylphosphonous acid which is then esterified and thereafter reacted with acrylic ester (DE-A-101 53 780).

Monocarboxy-functionalized dialkylphosphinic esters are also obtainable by reaction of bis(trimethylsilyl)phosphonite —HP(OSiMe$_3$)$_2$— with α,β-unsaturated carboxylic acid components, subsequent alkylation with alkyl halides by the Arbuzov reaction and alcoholysis (Kurdyumova, N. R.; Rozhko, L. F.; Ragulin, V. V.; Tsvetkov, E. N.; Russian Journal of General Chemistry (Translation of Zhurnal Obshchei Khimii (1997), 67(12), 1852-1856). The bis(trimethylsilyl) phosphonite ester is obtained from potassium or ammonium hypophosphite by reaction with hexamethyldisilazane.

Hitherto there are no methods in existence for producing monocarboxy-functionalized dialkylphosphinic acids, esters and salts that are available economically and on a large industrial scale and more particularly enable a high space-time yield to be achieved. Nor are there any methods that are sufficiently effective without unwelcome halogen compounds as starting materials, nor any where the end products are easy to obtain or isolate or else obtainable in a specific and desirable manner under controlled reaction conditions (such as a transesterification for example).

We have found that this object is achieved by a method for producing monocarboxy-functionalized dialkylphosphinic acids, esters and salts, which comprises a) reacting a phosphinic acid source (I)

with olefins (IV)

in the presence of a catalyst A to form an alkylphosphonous acid salt or ester (II)

b) reacting the resulting alkylphosphonous acid salt or ester (II) with an acrylonitrile (V)

in the presence of a catalyst B to form the monofunctionalized dialkylphosphinic acid derivative (VI)

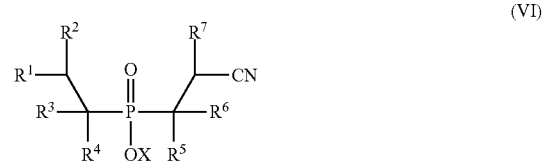

and c) reacting the monofunctionalized dialkylphosphinic acid derivative (VI) in the presence of a catalyst C to form the monocarboxy-functionalized dialkylphosphinic acid derivative (III)

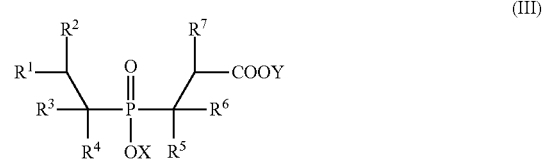

where $R^1$, $R^2$, $R^3$, $R^4$, $R^5$, $R^6$, $R^7$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl CN, CHO, OC(O)$CH_2CN$, CH(OH)$C_2H_5$, $CH_2CH(OH)CH_3$, 9-anthracene, 2-pyrrolidone, $(CH_2)_mOH$, $(CH_2)_mNH_2$, $(CH_2)_mNCS$, $(CH_2)_mNC(S)NH_2$, $(CH_2)_mSH$, $(CH_2)_m$S-2-thiazoline, $(CH_2)_mSiMe_3$, $C(O)R^8$, $(CH_2)_mC(O)R^8$, $CH=CH-R^8$ and/or $CH=CH-C(O)R^8$ where $R^8$ is $C_1$-$C_8$-alkyl or $C_6$-$C_{18}$-aryl and m is an integer from 0 to 10 and X and Y are identical or different and are each independently H, $C_1$-$C_{15}$-alkyl, $C_6$-$C_{18}$-aryl, $C_6$-$C_{18}$-aralkyl, $C_6$-$C_{18}$-alkylaryl, $(CH_2)_kOH$, $CH_2-CHOH-CH_2OH$, $(CH_2)_kO(CH_2)_kH$, $(CH_2)_k-CH(OH)-(CH_2)_kH$, $(CH_2-CH_2O)_kH$, $(CH_2-C[CH_3]HO)_kH$, $(CH_2-C[CH_3]HO)_k(CH_2-CH_2O)_kH$, $(CH_2-CH_2O)_k(CH_2-C[CH_3]HO)H$, $(CH_2-CH_2O)_k$-alkyl, $(CH_2-C[CH_3]HO)_k$-alkyl, $(CH_2-C[CH_3]HO)_k(CH_2-CH_2O)_k$-alkyl, $(CH_2-CH_2O)_k(CH_2-C[CH_3]HO)$O-alkyl, $(CH_2)_k-CH=CH(CH_2)_kH$, $(CH_2)_kNH_2$, $(CH_2)_kN[(CH_2)_kH]_2$, where k is an integer from 0 to 10, and/or Mg, Ca, Al, Sb, Sn, Ge, Ti, Fe, Zr, Zn, Ce, Bi, Sr, Mn, Cu, Ni, Li, Na, K, H and/or a protonated nitrogen base and the catalysts A comprise transition metals and/or transition metal compounds and/or catalyst systems composed of a transition metal and/or transition metal compound and at least one ligand, and the catalyst B comprises peroxide-forming compounds and/or peroxo compounds and/or comprises azo compounds and/or comprises alkali hydrides and/or alkaline earth metal hydrides and/or alkali alkoxides and/or alkaline earth metal alkoxides and the catalyst C comprises an acid or a base.

Preferably, the monocarboxy-functionalized dialkylphosphinic acid, its salt or ester (III) obtained after step c) is subsequently reacted in a step d) with metal compounds of Mg, Ca, Al, Sb, Sn, Ge, Ti, Fe, Zr, Zn, Ce, Bi, Sr, Mn, Li, Na, K and/or a protonated nitrogen base to form the corresponding monocarboxy-functionalized dialkylphosphinic acid salts (III) of these metals and/or of a nitrogen compound.

Preferably, the alkylphosphonous acid, salt or ester (II) obtained after step a) and/or the monofunctionalized dialkylphosphinic acid, salt or ester (VI) obtained after step b) and/or the monocarboxy-functionalized dialkylphosphinic acid, salt or ester (III) obtained after step c) and/or the particular resulting reaction solution thereof are esterified with an alkylene oxide or an alcohol M-OH and/or M'-OH, and the respectively resulting alkylphosphonous ester (II), monofunctionalized dialkylphosphinic ester (VI) and/or monocarboxy-functionalized dialkylphosphinic ester (III) are subjected to the further reaction steps b), c) or d).

Preferably, the groups $C_6$-$C_{18}$-aryl, $C_6$-$C_{18}$-aralkyl and $C_6$-$C_{18}$-alkylaryl are substituted with $SO_3X_2$, $-C(O)CH_3$, OH, $CH_2OH$, $CH_3SO_3X_2$, $PO_3X_2$, $NH_2$, $NO_2$, $OCH_3$, SH and/or $OC(O)CH_3$.

Preferably, $R^1$, $R^2$, $R^3$, $R^4$, $R^5$, $R^6$, $R^7$ are identical or different and are each independently H, methyl, ethyl, n-propyl, isopropyl, n-butyl, isobutyl, tert-butyl and/or phenyl.

Preferably, X and Y are identical or different and are each H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, ally and/or glycerol.

Preferably m=1 to 10 and k=2 to 10.

Preferably, the catalyst system A is formed by reaction of a transition metal and/or of a transition metal compound and at least one ligand.

Preferably, the transition metals and/or transition metal compounds comprise such from the seventh and eighth transition groups.

Preferably, the transition metals and/or transition metal compounds comprise rhodium, nickel, palladium, platinum and/or ruthenium.

Preferably, the catalyst B comprises hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide and/or peroxodisulfuric acid and/or comprises azobisisobutyronitrile, 2,2'-azobis(2-amidinepropane) dihydrochloride and/or 2,2'-azobis(N,N' dimethyleneisobutyramidine) dihydrochloride and/or comprises lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide and/or potassium butoxide.

Preferably, the catalyst C comprises metals, metal hydrides, metal hydroxides and metal alkoxides and mineral acids, for example sulfuric acid, nitric acid, hydrochloric acid, phosphoric acid or mixtures thereof.

Preferably, the acrylonitrile (V) comprise acrylonitrile, methylacrylonitrile, ethyl-2-cyanoacrylate, 3-phenylacrylonitrile, 2-methyl-2-butenenitrile.

Preferably, the alcohol of the general formula M-OH comprises linear or branched, saturated and unsaturated, monohydric organic alcohols having a carbon chain length of $C_1$-$C_{18}$ and the alcohol of the general formula M'-OH comprises linear or branched, saturated and unsaturated polyhydric organic alcohols having a carbon chain length of $C_1$-$C_{18}$.

The present invention also provides for the use of monocarboxy-functionalized dialkylphosphinic acids, esters and salts obtained according to one or more of claims 1 to 12 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, in washing and cleaning applications and in electronic applications.

The present invention likewise provides for the use of monocarboxy-functionalized dialkylphosphinic acids, salts and esters obtained according to one or more of claims 1 to 12 as a flame retardant, more particularly as a flame retardant for clearcoats and intumescent coatings, as a flame retardant for wood and other cellulosic products, as a reactive and/or non-reactive flame retardant for polymers, in the manufacture of flame-retardant polymeric molding materials, in the manufacture of flame-retardant polymeric molded articles and/or for flame-retardant finishing of polyester and cellulose straight and blend fabrics by impregnation.

The present invention additionally provides a flame-retardant thermoplastic or thermoset polymeric molding material containing 0.5% to 45% by weight of monocarboxy-functionalized dialkylphosphinic acids, salts or esters obtained according to one or more of claims 1 to 12, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

Moreover, the invention also provides flame-retardant thermoplastic or thermoset polymeric molded articles, films, threads and fibers containing 0.5% to 45% by weight of monocarboxy-functionalized dialkylphosphinic acids, salts or esters obtained according to one or more of claims 1 to 12, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

All the aforementioned reactions can also be carried out in stages; similarly, the various processing steps can also utilize the respective resulting reaction solutions.

When the monocarboxy-functionalized dialkylphosphinic acid (III) after step c) comprises an ester, an acidic or basic hydrolysis may preferably be carried out in order that the free monocarboxy-functionalized dialkylphosphinic acid or salt may be obtained.

Preferably, the monocarboxy-functionalized dialkylphosphinic acid comprises 3-(ethylhydroxyphosphinyl)propionic acid, 3-(propylhydroxyphosphinyl)propionic acid, 3-(i-propylhydroxyphosphinyl)propionic acid, 3-(butylhydroxyphosphinyl)-propionic acid, 3-(sec-butylhydroxyphosphinyl)propionic acid, 3-(1-butyl-hydroxyphosphinyl)propionic acid, 3-(2-phenylethylhydroxyphosphinyl)propionic acid, 3-(ethylhydroxyphosphinyl)-2-methylpropionic acid, 3-(propylhydroxyphosphinyl)-2-methylpropionic acid, 3-(i-propylhydroxyphosphinyl)-2-methylpropionic acid, 3-(butylhydroxyphosphinyl)-2-methylpropionic acid, 3-(sec-butylhydroxyphosphinyl)-2-methylpropionic acid, 3-(1-butylhydroxyphosphinyl)-2-methylpropionic acid, 3-(2-phenylethylhydroxyphosphinyl)-2-methylpropionic acid, 3-(ethylhydroxyphosphinyl)-3-phenylpropionic acid, 3-(propylhydroxy-phosphinyl)-3-phenylpropionic acid, 3-(i-propylhydroxyphosphinyl)-3-phenyl-propionic acid, 3-(butylhydroxyphosphinyl)-3-phenylpropionic acid, 3-(i -butyl-hydroxyphosphinyl)-3-phenylpropionic acid, 3-(sec-butylhydroxyphosphinyl)-3-phenylpropionic acid, 3-(2-phenylethylhydroxyphosphinyl)-3-phenylpropionic acid.

Preferably, the target compounds to be prepared also comprise monocarboxy-functionalized dialkylphosphinic esters such as propionic acid, methyl, ethyl; i-propyl; butyl, phenyl; 2-hydroxyethyl, 2-hydroxypropyl, 3-hydroxypropyl, 4-hydroxybutyl and/or 2,3-dihydroxypropyl ester of the aforementioned monocarboxy-functionalized dialkylphosphinic acids or mixtures thereof.

Preferably, the target compounds to be prepared also comprise monocarboxy-functionalized dialkylphosphinic salts such as aluminum(III), calcium(II), magnesium(II), cerium (III), titanium(IV) and/or zinc(II) salts of the aforementioned monocarboxy-functionalized dialkylphosphinic acids or of the aforementioned monocarboxy-functionalized dialkylphosphinic esters.

Target compounds also include those esters and salts where the esterification and salt formation, respectively, takes place on the phosphinic acid group (at X in formula (III)) or on the propionic acid group (at Y in formula (III)).

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium and platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropane-sulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal salt is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 µm).

Preferably, the transition metal is used supported on a metal oxide such as, for example, alumina, silica, titanium dioxide, zirconium dioxide, zinc oxide, nickel oxide, vanadium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™ on functionalized polysiloxanes such as, for example, Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or moe complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene.

Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), Z-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

platinum(II) chloride, platinum(II) bromide, platinum(II) iodide, platinum(II) fluoride, platinum(II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum (II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine 2,2':6',2"-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocya-nine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(1) dimer, (2-methylallyl)palladium(II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane]palladium(0), bis(3,5,3',5'-dimethoxydibenzylideneacetone)palladium(0), bis(tri-tert-butyl phosphine)palladium(0), meso-tetraphenyltetrabenzoporphinepalladium, tetrakis(methyldiphenylphosphine)palladium(0), tris(3,3',3"-phosphinidyne-tris(benzenesulfonato)palladium(0) nonasodium salt, 1,3-bis(2,4,6-trimethyl-1-phenyl)imidazol-2-ylidene(1,4-naphthoquinone)palladium(0), 1,3-bis(2,6-diisopropylphenyl)imidazol-2-ylidene(1,4-naphthoquinone)palladium(0) and the chloroform complex thereof;

allylnickel(II) chloride dimer, ammoniumnickel(II) sulfate, bis(1,5-cycloocta-diene)nickel(0), bis(triphenylphosphine)dicarbonylnickel(0), tetrakis(triphenyl-phosphine)nickel(0), tetrakis(triphenyl phosphite)nickel(0), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate(IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diammintetrachloroplatinum(IV), potassium trichloro(ethylene)platinate(II), sodium hexahydroxyplatinate(IV), tetraamineplatinum(II) tetrachloroplatinate(II), tetrabutylammonium hexachloroplatinate(IV), ethylenebis(triphenylphosphine)platinum(0), platinum(0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum (0), platinum octaethylporphyrine, chloroplatinic acid, carboplatin;

chlorobis(ethylene)rhodium dimer, hexarhodium hexadecacarbonyl, chloro(1,5-cyclooctadiene)rhodium dimer, chloro(norbornadiene)rhodium dimer, chloro(1,5-hexadiene) rhodium dimer.

The ligands preferably comprise phosphines of the formula (VII)

$$PR^9_3 \quad (VII)$$

where the $R^9$ radicals are each independently hydrogen, straight-chain, branched or cyclic $C_1$-$C_{20}$-alkyl, $C_1$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives and/or phenyl substituted by at least one $R^{10}$, or naphthyl substituted by at least one $R^{10}$. $R^{10}$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO(C_1$-$C_{20}$-alkyl), $NHCO(C_1$-$C_{20}$-alkyl), $C_1$-$C_{20}$-Acyl, —$SO_3M$, —$SO_2N(R^{11})M$, —$CO_2M$, —$PO_3M_2$, -$AsO_3M_2$, —$SiO_2M$, —$C(CF_3)_2OM$ (M=H, Li, Na or K), where $R^{11}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, silyl and/or their derivatives, aryl, $C_1$-$C_{20}$-arylalkyl, $C_1$-$C_{20}$-alkylaryl, phenyl and/or biphenyl. Preferably, the $R^9$ groups are all identical.

Suitable phosphines(VII) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethyl-phosphine, phenyldimethylphosphine, tri(o-tolyl)phosphine, tri(p-tolyl) phosphine, ethyldiphenylphosphine, dicyclohexylphenylphosphine, 2-pyridyl-diphenylphosphine, bis(6-methyl-2-pyridyl)phenylphosphine, tri(p-chlorophenyl)-phosphine, tri(p-methoxyphenyl)phosphine, diphenyl(2-sulfonatophenyl)-phosphine; potassium, sodium and ammonium salts of diphenyl(3-sulfonato-phenyl)phosphine, bis(4,6-dimethyl-3-sulfonatophenyl)(2,4-dimethylphenyl)phosphine, bis(3-sulfonatophenyl)phenylphosphines, tris(4,6-dimethyl-3-sulfonatophenyl)phosphines, tris (2-sulfonatophenyl)phosphines, tris(3-sulfonato-phenyl) phosphines; 2-bis(diphenylphosphinoethyl) trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the general formula $$R^9M''-Z-M''R^9 \quad (VIII).$$

In this formula, each M'' independently is N, P, As or Sb. M'' is preferably the same in the two occurrences and more preferably is a phosphorus atom.

Each $R^9$ group independently represents the radicals described under formula (VIII). The $R^9$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—$O$—$CH_2$—, —$CH_2$—$CH_2$—$CH_2$—$CH_2$—, —$CH_2$—$CH(C_2H_5)$—$CH_2$—, —$CH_2$—$CH(n-Pr)$-$CH$ and —$CH_2$—$CH(n-Bu)$—$CH_2$—, substituted or unsubstituted 1,2-phenyl, 1,2-cyclohexyl, 1,1''- or 1,2-ferrocenyl radicals, 2,2''-(1,1''-biphenyl), 4,5-xanthene and/or oxydi-2,1-phenylene radicals.

Examples of suitable bidentate phosphine ligands (VIII) are for example 1,2-bis(dimethylphosphino)ethane, 1,2-bis (diethylphosphino)ethane, 1,2-bis(dipropylphosphino) ethane, 1,2-bis(diisopropylphosphino)ethane, 1,2-bis(dibutylphosphino)ethane, 1,2-bis(di-tert-butylphosphino)ethane, 1,2-bis(dicyclohexylphosphino)ethane, 1,2-bis(diphenylphosphino)ethane; 1,3-bis(dicyclohexylphosphino)propane, 1,3-bis(diisopropylphosphino)propane, 1,3-bis(di-tert-butylphosphino)propane, 1,3-bis(diphenylphosphino) propane; 1,4-bis(diisopropylphosphino)butane, 1,4-bis (diphenylphosphino)butane; 1,5-bis (dicyclohexylphosphino)pentane; 1,2-bis(di-tert-butylphosphino)benzene, 1,2-bis(diphenylphosphino) benzene, 1,2-bis(dicyclohexylphosphino)benzene, 1,2-bis (dicyclopentylphosphino)benzene, 1,3-bis(di-tert-butylphosphino)benzene, 1,3-bis(diphenylphosphino) benzene, 1,3-bis(dicyclohexylphosphino)benzene, 1,3-bis (dicyclopentylphosphino)benzene; 9,9-dimethyl-4,5-bis (diphenylphosphino)-xanthene, 9,9-dimethyl-4,5-bis (diphenylphosphino)-2,7-di-tert-butylxanthene, 9,9-dimethyl-4,5-bis(di-tert-butylphosphino)xanthene, 1,1'-bis (diphenylphosphino)-ferrocene, 2,2'-bis (diphenylphosphino)-1,1'-binaphthyl, 2,2'-bis(di-p-tolylphosphino)-1,1'-binaphthyl, (oxydi-2,1-phenylene)bis (diphenylphosphine), 2,5-(diisopropylphospholano) benzene, 2,3-O-isopropylidene-2,3-dihydroxy-1,4-bis (diphenylphosphino)butane, 2,2'-bis(di-tert-butylphosphino)-1,1'-biphenyl, 2,2'-bis (dicyclohexylphosphino)-1,1'-biphenyl, 2,2'-bis (diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonato-phenyl)phosphino]methyl]-4,4',7, 7'-tetrasulfonato-1,1'-binapthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino] methyl]-1,1'-binapthyl, (2,2'-bis[[bis(3-sulfonatophenyl) phosphino]methyl]-1,1'-biphenyl, 9,9-dimethyl-4,5-bis (diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)-benzene, meso-tetrakis (4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl) porphine and 5,11,17,23-sulfonato-25,26,27,28-tetrahydroxycalix[4]arene.

Moreover, the ligands of the formula (VII) and (VIII) can be attached to a suitable polymer or inorganic substrate by the $R^9$ radicals and/or the bridging group.

The molar transition metal/ligand ratio of the catalyst system is in the range 1:0.01 to 1:100, preferably in the range from 1:0.05 to 1:10 and more preferably in the range from 1:1 to 1:4.

The reactions in the process stages a), b) c) and d) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the transition metal and/or the transition metal compound and/or catalyst system and/or the ligand and/or starting materials are optionally isolated after the process stages a), b) c) and d) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) c) and d) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 kW/m$^3$, preferably 0.30-1.65 kW/m$^3$.

During the reaction, the catalyst A is preferably homogeneous and/or heterogeneous in action. Therefore, the particular heterogeneous catalyst is effective during the reaction as a suspension or bound to a solid phase.

Preferably, the catalyst A is generated in situ before the reaction and/or at the start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or in supercritical phase. The catalyst A is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

Preferably, $R^1$, $R^2$, $R^3$ and $R^4$ of olefin (IV) are the same or different and each is independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsillane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and 1-vinyl-2-pyrrolidone.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably in the range from 1:0.01 to 1:0.000001.

The phosphinic acid/solvent molar ratio for the reaction is preferably in the range from 1:10 000 to 1:0 and more preferably in the range from 1:50 to 1:1.

One method the present invention provides for producing compounds of the formula (II) comprises reacting a phosphinic acid source with olefins in the presence of a catalyst and freeing the product (II) (alkylphosphonous acid, salts or esters) of catalyst, transition metal or transition metal compound as the case may be, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex® QuadraPure™, Smopex®, Poly-Orgs®; polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliary 2 is preferably the aforementioned solvent of the present invention as are preferably used in process stage a).

The esterification of the monocarboxy-functionalized dialkylphosphinic acid (III) or of the monofunctionalized dialkylphosphinic acid (VI) or of the alkylphosphonous acid derivatives (II) and also of the phosphinic acid source (I) to form the corresponding esters can be achieved for example by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the general formula M-OH and/or M'-OH or by reaction with alkylene oxides, as indicated hereinbelow.

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also useful as M-OH and M'-OH are mono- or polyhydric unsaturated alcohols having a carbon chain length of $C_1$-$C_{18}$, for example n-but-2-en-1-ol, 1,4-butenediol and allyl alcohol.

Also useful as M-OH and M'-OH are reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethylhexyloxy)ethanol, 2-n-dodecoxyethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Useful M-OH and M'-OH further include reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also useful as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanolamine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxy-butane, 1,2-epoxyethylbenzene, (2,3-epoxypropyl)benzene, 2,3-epoxy-1-propanol and 3,4-epoxy-1-butene.

Suitable solvents are the solvents mentioned in the process step a) and the M-OH and M'-OH alcohols used and the alkylene oxides. These offer advantages in the form of a higher space-time yield.

The reaction is preferably carried out under the autogenous vapor pressure of the employed alcohol M-OH, M'-OH and alkylene oxide and/or of the solvent.

Preferably, the reaction is carried out at a partial pressure of the employed alcohol M-OH, M'-OH and alkylene oxide of 0.01-100 bar, more preferably at a partial pressure of the alcohol of 0.1-10 bar.

The reaction is preferably carried out at a temperature in the range from −20 to 340° C. and is more preferably carried out at a temperature in the range from 20 to 180° C.

The reaction is preferably carried out at a total pressure in the range from 1 to 100 bar.

The reaction is preferably carried out in a molar ratio for the alcohol or alkylene oxide component to the phosphinic acid source (I) or alkylphosphonous acid (II) or monofunctionalized dialkylphosphinic acid (VI) or monocarboxy-functionalized dialkylphosphinic acid (III) ranging from 10 000:1 to 0.001:1 and more preferably from 1000:1 to 0.01:1.

The reaction is preferably carried out in a molar ratio for the phosphinic acid source (I) or alkylphosphonous acid (II) or monofunctionalized dialkylphosphinic acid (VI) or monocarboxy-functionalized dialkylphosphinic acid (III) to the solvent ranging from 1:10 000 to 1:0 and more preferably in a phosphinic acid/solvent molar ratio ranging from 1:50 to 1:1.

Particularly preferred catalysts B as used in process stage b) are peroxo compounds such as peroxomonosulfuric acid, potassium monopersulfate (potassium peroxomonosulfate), Caroat™, Oxone™, peroxodisulfuric acid, potassium persulfate (potassium peroxodisulfate), sodium persulfate (sodium peroxodisulfate), ammonium persulfate (ammonium peroxodisulfate).

Particularly preferred catalysts B are compounds capable of forming peroxides in the solvent system, such as sodium peroxide, sodium peroxide hydrates, lithium peroxide, lithium peroxide hydrates, calcium peroxide, strontium peroxide, barium peroxide, magnesium peroxide, zinc peroxide, potassium hyperoxide, potassium hyperoxide hydrates, sodium peroxoborate, sodium peroxoborate hydrates, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Preferred catalysts B are hydrogen peroxide, performic acid, peracetic acid, benzoyl peroxide, di-t-butyl peroxide, dicumyl peroxide, 2,4-di-chlorobenzoyl peroxide, decanoyl peroxide, lauryl peroxide, cumene hydroperoxide, pinene hydroperoxide, p-menthane hydroperoxide, t-butyl hydroperoxide, acetylacetone peroxide, methyl ethyl ketone peroxide, succinic acid peroxide, dicetyl peroxydicarbonate, t-butyl peroxyacetate, t-butylperoxymaleic acid, t-butyl peroxybenzoate, acetyl cyclohexylsulfonyl peroxide.

Preferred catalysts B are water-soluble azo compounds. Particular preference is given to azo initiators such as VAZO® 52 2,2'-azobis(2,4-dimethylvaleronitrile), VAZO® 64 (azobisisobutyronitrile), AIBN), VAZO® 67 2,2'-azobis(2-methyl-butyronitrile), VAZO® 88 1,1'-azobis(cyclohexane-1-carbonitrile), VAZO® 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methyl-propionate), V-59 2,2'-azobis(2-methylbutyronitrile), V-40 1,1'-azobis(cyclohexane-1-carbonitrile), VF-096 2,2'-azobis[N-(2-propenyl)-2-methylpropionamide], V-30 1-[(cyano-1-methylethyl)azo]formamide, VAm-110 2,2'-azobis(N-butyl-2-methyl-propionamide), VAm-111 2,2'-azobis(N-cyclohexyl-2-methylpropionamide), VA-046B 2,2'-azobis[2-(2-imidazolin-2-yl)propane disulfate dihydrates, VA-057 2,2'-azobis[N-(2-carboxyethyl)-2-methylpropionamidine]tetrahydrate, VA-061 2,2'-azobis[2-(2-imidazolin-2-yl)propane], VA-080 2,2'-azobis{2-methyl-N-[1,1-bis(hydroxymethyl)-2-hydroxyethyl] propionamide, VA-085 2,2'-azobis{2-methyl-N-[2-(1-hydroxybutyl)]propionamide}, VA-086 2,2'-azobis[2-methyl-N-(2-hydroxy-ethyl)propionamide] from Wako Chemicals.

It is also possible to use azo initiators such as 2-tert-butylazo-2-cyanopropane, dimethyl azodiisobutyrate, azodiisobutyronitrile, 2-tert-butylazo-1-cyano-cyclohexane, 1-tert-amylazo-1-cyanocyclohexane. Preference is further given to alkyl perketals such as 2,2-bis-(tert-butylperoxy) butane, ethyl 3,3-bis(tert-butyl-peroxy)butyrate, 1,1-di(tert-butylperoxy)cyclohexane.

Preferred catalysts B are also metals, metal hydrides and metal alkoxides such as, for example, lithium, lithium hydride, lithium aluminohydride, methyllithium, butyllithium, tert-butyllithium, lithium diisopropylamide, sodium, sodium hydride, sodium borohydride, sodium methoxide, sodium ethoxide, sodium butoxide, potassium methoxide, potassium ethoxide or potassium butoxide.

The catalyst B is preferably used in amounts of 0.05 to 5 mol % based on the respective acrylonitriles (V).

The catalyst B is preferably used in amounts of 0.001 to 10 mol %, based on the phosphorus-containing compound.

Suitable solvents are those used above in process stage a).

The catalyst B is preferably metered in at a rate of 0.01 to 10 mol % of catalyst per hour, based on the phosphorus-containing compound.

The reaction of the alkylphosphonous acids (II) with the acrylonitrile (V) is preferably carried out at a temperature of 0 to 250° C., more preferably at 20 to 200° C. and more particularly at 50 to 150° C.

The atmosphere for the reaction with the acrylonitrile (V) preferably consists of constituents of the solvent and acrylonitrile to an extent of 50% to 99.9% by weight, preferably 70-95%.

The reaction during the addition of acrylonitrile (V) is preferably carried out at a pressure of 1-20 bar.

In a further embodiment of the method, the product mixture obtained after process stage a) and/or b) is worked up.

In a further embodiment of the method, the product mixture obtained after process stage a) is worked up and thereafter the monofunctionalized dialkylphosphinic acids and/or their esters and alkali metal salts obtained after process stage b) are reacted in process stage c).

The invention further provides a method in step b) for continuous production of monofunctionalized dialkylphosphinic esters (VI) by reaction of alkylphosphonous esters (II) with acrylonitrile (V) in the presence of metal alkoxides (catalyst B), which method comprises a) initially charging a self-contained reactor configured to circulate the reaction mixture and equipped with cooling means and also an overflow with a volume corresponding to the reactor volume of the monofunctionalized dialkylphosphinic esters (VI) to be produced, optionally mixed with the alcohol corresponding to the metal alkoxide as solvent, and recirculating, b) the alkylphosphonous ester (II), the acrylonitrile (V) and also an alcoholic solution of the metal alkoxide being continuously introduced into the reactor with cooling of the recirculated reactor contents, and reacted at a temperature of about 0 to 80° C. in the course of about 5-120 minutes, wherein the molar ratio of the alkylphosphonous ester (II) to the acrylonitrile (V) is about 1:0.9-2 and the amount of the metal alkoxide, based on the alkylphosphonous ester (II), is about 0.1 to 5 mol %; and c) continuously withdrawing, over the overflow of the reactor, a mixture comprising the process product and separating the monofunctionalized dialkyl-phosphinic ester (VI) from the mixture by distillation.

In a preferred embodiment of the method according to the present invention, the reaction of the reaction components is carried out at a temperature of 20 to 50° C.

The charging of the reactor with the reaction components and the catalyst solution can be carried out for example by a) passing the alkylphosphonous ester (II), the acrylonitrile (V) and also the alcoholic solution of the metal alkoxide into the reactor separately,
b) passing a mixture of the alkylphosphonous ester (II) with the acrylonitrile (V) into the reactor separately from the alcoholic solution of the metal alkoxide, or
c) passing a mixture of the alkylphosphonous ester (II) with the alcoholic solution of the metal alkoxide into the reactor separately from the acrylonitrile (V).

It is further advantageous when the alcohol used as solvent and/or the alcoholic component of the metal alkoxide correspond to the alcoholic component of the alkylphosphonous ester (II).

When alkylphosphonous ester (II) and the alcoholic metal alkoxide solution are used with different alcoholic components, a mixed product will be obtained as process product.

Lastly, preferred features of the invention consist in the molar ratio of alkylphosphonous ester (II) to acrylonitrile (V) being in the range from 1:1-1.3, the amount of catalyst B based on the alkylphosphonous ester (II) being 1-5 mol % and the amount of alcohol used as solvent being 0.1-1000 mol per mole of alkylphosphonous ester (II).

The method of the present invention makes it possible to produce monofunctionalized dialkylphosphinic ester (VI) continuously on an industrial scale in a hitherto unattained yield of about 90% of theory.

The step c) conversion to the monocarboxy-functionalized dialkylphosphinic acid, salts and esters (III) is achieved by acidic or alkaline hydrolysis of the monofunctionalized dialkylphosphinic acid, salts or esters (VI) using acids or bases in the presence of water by removing the resulting ammonium salt or ammonia.

When a monocarboxy-functionalized dialkylphosphinic acid salt (III) is obtained, it can be reacted with a mineral acid to form the corresponding acid and be esterified with an alcohol M-OH or M'-OH or an alkylene oxide.

When a monocarboxy-functionalized dialkylphosphinic acid ammonium salt (III) is obtained, it can first be reacted with a base to form a monocarboxy-functionalized dialkylphosphinic acid salt (III) which are then reacted with a mineral acid to form the corresponding acid and esterified with an alcohol M-OH or M'-OH or an alkylene oxide.

Suitable mineral acids are for example hydrochloric acid, sulfuric acid, nitric acid or phosphoric acid or mixtures thereof.

Suitable bases are the metals, metal hydrides and metal alkoxides mentioned as catalysts B, for example lithium, lithium hydride, lithium aluminohydride, methyllithium, butyllithium, t-butyllithium, lithium diisopropylamide, sodium, sodium hydride, sodium borohydride, sodium methoxide, sodium ethoxide or sodium butoxide, potassium methoxide, potassium ethoxide or potassium butoxide and also sodium hydroxide, potassium hydroxide, lithium hydroxide, barium hydroxide.

The acidic or alkaline hydrolysis may preferably be carried out in the presence of water and an inert solvent. Suitable inert solvents are the solvents mentioned in process step a), preference being given to low molecular weight alcohols having 1 to 6 carbon atoms. The use of saturated aliphatic alcohols is particularly preferred. Examples of suitable alcohols are methanol, ethanol, propanol, i-propanol, butanol, 2-methyl-1-propanol, n-pentanol, 2-pentanol, 3-pentanol, 2-methyl-2-butanol, 3-methyl-2-butanol, 2-methyl-3-butanol, 3-methyl-1-butanol or 2-methyl-1-butanol.

Preferred bases (catalyst C) for carrying out the alkaline hydrolysis are the metals, metal hydrides and metal alkoxides mentioned as catalysts B such as for example lithium, lithium hydride, lithium aluminohydride, methyllithium, butyllithium, t-butyllithium, lithium diisopropylamide, sodium, sodium hydride, sodium borohydride, sodium methoxide, sodium ethoxide or sodium butoxide, potassium methoxide, potassium ethoxide or potassium butoxide and also sodium hydroxide, potassium hydroxide, lithium hydroxide, barium hydroxide, ammonium hydroxide. Preference is given to using sodium hydroxide, potassium hydroxide and barium hydroxide.

Preferred mineral acids (catalyst C) for carrying out the acidic hydrolysis are for example sulfuric acid, nitric acid, hydrochloric acid, phosphoric acid or mixtures thereof. Preference is given to using sulfuric acid or hydrochloric acid.

The presence of water is essential to carrying out the hydrolysis. The amount of water can range from the stoichiometric requirement as minimum level to an excess.

The hydrolysis is preferably carried out in a phosphorus/water molar ratio of 1:1 to 1:1000 and more preferably in the range from 1:1 to 1:10.

The hydrolysis is preferably carried out in a phosphorus/base or acid molar ratio of 1:1 to 1:300 and more preferably in the range from 1.1 to 1:20.

The amount of alcohol used is generally in the range from 0.5 kg to 1.5 kg per kg of the monofunctionalized dialkylphosphinic acid, salts or esters (VI), preferably in the range from 0.6 kg to 1.0 kg.

The reaction temperature is in the range from 50° C. to 140° C. and preferably in the range from 80° C. to 130° C.

The reaction is preferably carried out at a total pressure in the range from 1 to 100 bar and more preferably at a total pressure in the range from 1 to 10 bar.

The reaction time is in the range from 0.2 to 20 hours and more preferably in the range from 1 to 12 hours.

In one particular embodiment, the monofunctionalized dialkylphosphinic acid, salt or ester (VI) is hydrolyzed with an aqueous barium hydroxide solution to the barium salt of the corresponding monocarboxy-functionalized dialkylphosphinic acid (III) and thereafter reacted with ammonium carbonate or preferably with ammonia followed by carbon dioxide to form the ammonium salt of the monocarboxy-functionalized dialkylphosphinic acid (III) and barium carbonate. The latter can be converted thermally into the free monocarboxy-functionalized dialkylphosphinic acid (III) and ammonia.

The monocarboxy-functionalized dialkylphosphinic acid or salt (III) can thereafter be converted into further metal salts.

The metal compounds which are used in process stage d) preferably comprise compounds of the metals Mg, Ca, Al, Sb, Sn, Ge, Ti, Fe, Zr, Zn, Ce, Bi, Sr, Mn, Li, Na, K, more preferably Mg, Ca, Al, Ti, Zn, Sn, Ce, Fe.

Suitable solvents for process stage d) are those used above in process stage a).

The reaction of process stage d) is preferably carried out in an aqueous medium.

Process stage d) preferably comprises reacting the monocarboxy-functionalized dialkylphosphinic acids, esters and/or alkali metal salts (III) obtained after process stage c) with metal compounds of Mg, Ca, Al, Zn, Ti, Sn, Zr, Ce or Fe to form the monocarboxy-functionalized dialkylphosphinic acid salts (III) of these metals.

The reaction is carried out in a molar ratio of monocarboxy-functionalized dialkylphosphinic acid, ester or salt (III) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, monocarboxy-functionalized dialkylphosphinic acid, ester or salt (III) obtained in process stage c) is converted into the corresponding dialkylphosphinic acid and the latter is reacted in process stage d) with metal compounds of Mg, Ca, Al, Zn, Ti, Sn, Zr, Ce or Fe to form the monocarboxy-functionalized dialkylphosphinic acid salts (III) of these metals.

Preferably, monocarboxy-functionalized dialkylphosphinic acid/ester (III) obtained in process stage c) is converted to a dialkylphosphinic acid alkali metal salt and the latter is reacted in process stage d) with metal compounds of Mg, Ca, Al, Zn, Ti, Sn, Zr, Ce or Fe to form the monocarboxy-functionalized dialkylphosphinic acid salts (III) of these metals.

The metal compounds of Mg, Ca, Al, Zn, Ti, Sn, Zr, Ce or Fe for process stage d) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate, thiocyanate oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids such as, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts such as for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxoacids of transition metals (for example zinc chromate(VI) hydroxide, chromite, molybdate, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

In the case of titanium compounds, metallic titanium is as is titanium(III) and/or (IV) chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(II) fluoride, chloride and nitrate are also suitable.

In the case of zirconium compounds, metallic zirconium is preferred as are zirconium salts such as zirconium chloride, zirconium sulfate, zirconyl acetate, zirconyl chloride. Zirconium oxides and also zirconium (IV) tert-butoxide are also preferred.

The reaction in process stage d) is preferably carried out at a solids content of the monocarboxy-functionalized dialkylphosphinic acid salts in the range from 0.1% to 70% by weight, preferably 5% to 40% by weight.

The reaction in process stage d) is preferably carried out at a temperature of 20 to 250° C., preferably at a temperature of 80 to 120° C.

The reaction in process stage d) is preferably carried out at a pressure between 0.01 and 1000 bar, preferably 0.1 to 100 bar.

The reaction in process stage d) preferably takes place during a reaction time in the range from $1*10^{-7}$ to $1*10^2$ h.

Preferably, the monocarboxy-functionalized dialkylphosphinic acid salt (III) removed after process stage d) from the reaction mixture by filtration and/or centrifugation is dried.

Preferably, the product mixture obtained after process stage c) is reacted with the metal compounds without further purification.

Preferred solvents are the solvents mentioned in process step a).

The reaction in process stage d) and/or c) is preferably carried out in the solvent system given by stage a) and/or b).

The reaction in process stage d) is preferred in a modified given solvent system. Acidic components, solubilizers, foam inhibitors, etc are added for this purpose.

In a further embodiment of the method, the product mixture obtained after process stage a), b), c) and/or d) is worked up.

In a further embodiment of the method, the product mixture obtained after process stage c) is worked up and thereafter the monocarboxy-functionalized dialkylphosphinic acids and/or salts or esters (III) obtained after process stage c) are reacted in process stage d) with the metal compounds.

Preferably, the product mixture after process stage c) is worked up by isolating the monocarboxy-functionalized dialkylphosphinic acids and/or salts or esters (III) by removing the solvent system, for example by evaporation.

Preferably, the monocarboxy-functionalized dialkylphosphinic acid salt (III) of the metals Mg, Ca, Al, Zn, Ti, Sn, Zr, Ce or Fe selectively has a residual moisture content of 0.01% to 10% by weight, preferably of 0.1% to 1% by weight,
an average particle size of 0.1 to 2000 μm, preferably of 10 to 500 μm,
a bulk density of 80 to 800 g/l, preferably 200 to 700 g/l,
and a Pfrengle flowability of 0.5 to 10, preferably of 1 to 5.

The molded articles, films, threads and fibers more preferably contain from 5% to 30% by weight of the monocarboxy-functionalized dialkylphosphinic acid/ester/salts produced according to one or more of claims 1 to 12, from 5% to 90% by weight of polymer or mixtures thereof, from 5% to 40% by weight of additives and from 5% to 40% by weight of filler, wherein the sum total of the components is always 100% by weight.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, nucleus-forming agents, nucleating agents, additives for laser marking, hydrolysis stabilizers, chain extenders, color pigments, softeners, plasticizers and/or plasticizing agents.

Preference is given to a flame retardant containing 0.1 to 90% by weight of the monocarboxy-functionalized dialkylphosphinic acid, ester and salts (III) and 0.1% to 50% by weight, of further additives, more preferably diols.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

More particularly, the present invention provides for the use of the present invention monocarboxy-functionalized dialkylphosphinic acid, esters and salts (III) as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters are derived from dicarboxylic acids and their esters and diols and/or from hydroxyl carboxylic acids or the corresponding lactones.

It is particularly preferable to use terephthalic acid and ethylene glycol, 1,3-propanediol and 1,3-butanediol.

Suitable polyesters include inter alia polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Synthetic linear polyesters having permanent flame retardancy are composed of dicarboxylic acid components, diol components of the present invention monocarboxy-functionalized dialkylphosphinic acids and ester, or of the monocarboxy-functionalized dialkylphosphinic acids and esters produced by the method of the present invention as phosphorus-containing chain members. The phosphorus-containing chain members account for 2-20% by weight of the dicarboxylic acid component of the polyester. The resulting phosphorus content in the polymer is preferably 0.1-5%, more preferably 0.5-3% by weight.

The following steps can be carried out with or by addition of the compounds produced according to the present invention.

Preferably, the molding material is produced from the free dicarboxylic acid and diols by initially esterifying directly and then polycondensing.

When proceeding from dicarboxylic esters, more particularly dimethyl esters, it is preferable to first transesterify and then to polycondense by means of customary catalysts.

Polyester production may preferably proceed by adding customary additives (crosslinking agents, matting agents and stabilizing agents, nucleating agents, dyes and fillers, etc) in addition to the customary catalysts.

The esterification and/or transesterification involved in polyester production is preferably carried out at temperatures of 100-300° C., more preferably at 150-250° C.

The polycondensation involved in polyester production preferably takes place at pressures between 0.1 to 1.5 mbar and temperatures of 150-450° C., more preferably at 200-300° C.

The flame-retardant polyester molding materials produced according to the present invention are preferably used in polyester molded articles.

Preferred polyester molded articles are threads, fibers, self-supporting films/sheets and molded articles containing mainly terephthalic acid as dicarboxylic acid component and mainly ethylene glycol as diol component.

The resulting phosphorus content in threads and fibers produced from flame-retardant polyesters is preferably 0.1%-18%, more preferably 0.5%-15% by weight and in the case of self-supporting films/sheets 0.2%-15%, preferably 0.9%-12% by weight.

Suitable polystyrenes are polystyrene, poly(p-methylstyrene) and/or poly(alpha-methylstyrene).

Suitable polystyrenes preferably comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Suitable polystyrenes preferably also comprise graft copolymers of styrene or of alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are known for example as ABS, MBS, ASA or AES polymers.

The polymers also preferably comprise polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7, 7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont, Durethan® B 29, from Bayer and Grillamid®, from Ems Chemie, inter alia.

Also suitable are aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The monocarboxy-functionalized dialkylphosphinic acid/ester/salts produced according to one or more of claims 1 to 12 are preferably used in molding materials further used for producing polymeric molded articles.

It is particularly preferable for the flame-retardant molding material to contain from 5% to 30% by weight of monocarboxy-functionalized dialkylphosphinic acids, salts or esters produced according to one or more of claims 1 to 12, from 5% to 90% by weight of polymer or mixtures thereof, from 5% to 40% by weight of additives and 5% to 40% by weight of filler, wherein the sum total of the components is always 100% by weight.

The present invention also provides flame retardants containing monocarboxy-functionalized dialkylphosphinic acids, salts or esters produced according to one or more of claims 1 to 12.

The present invention also provides polymeric molding materials and also polymeric molded articles, films, threads and fibers containing the monocarboxy-functionalized dialkylphosphinic acid salts (III) of the metals Mg, Ca, Al, Zn, Ti, Sn, Zr, Ce or Fe produced according to the present invention.

The examples which follow illustrate the invention.

Production, processing and testing of flame-retardant polymeric molding materials and flame-retardant polymeric molded articles.

The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reiforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness. The UL 94 fire classifications are as follows:

V-0: Afterflame time never longer than 10 sec, total of afterflame times for 10 flame applications not more than 50 sec, no flaming drops, no complete consumption of the specimen, afterglow time for specimens never longer than 30 sec after end of flame application.

V-1: Afterflame time never longer than 30 sec after end of flame application, total of afterflame time for 10 flame applications not more than 250 sec, afterglow time for specimens never longer than 60 sec after end of flame application, other criteria as for V-0

V-2: Cotton indicator ignited by flaming drops, other criteria as for V-1

Not classifiable (ncl): does not comply with fire classification V-2.

Some investigated specimens were also tested for their LOI value. The LOI (Limiting Oxygen Index) value is determined according to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| LOI | 23 | flammable |
|---|---|---|
| LOI | 24-28 | potentially flammable |
| LOI | 29-35 | flame resistant |
| LOI | >36 | particularly flame-resistant |

Chemicals and abbreviations used

| VE water | completely ion-free water |
|---|---|
| AIBN | azobis(isobutyronitrile), (from WAKO Chemicals GmbH) |
| WakoV65 | 2,2'-azobis(2,4-dimethylvaleronitrile), (from WAKO Chemicals GmbH) |
| Deloxan ® THP II | metal scavenger (from Evonik Industries AG) |

Example 1

At room temperature, a three-neck flask equipped with stirrer and high-performance condenser is initially charged with 188 g of water and this initial charge is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and charged with ethylene under superatmospheric pressure while stirring and the reaction mixture is heated to 80° C. After 28 g of ethylene has been taken up, the system is cooled down and free ethylene is discharged. The reaction mixture is freed of solvent on a rotary evaporator. The residue is admixed with 100 g of VE water and at room temperature stirred under nitrogen, then filtered and the filtrate is extracted with toluene, thereafter freed of solvent on a rotary evaporator and the product is collected. Yield: 92 g (98% of theory) of ethylphosphonous acid.

Example 2

Example 1 is repeated with 99 g of phosphinic acid, 396 g of butanol, 42 g of ethylene, 6.9 mg of tris(dibenzylideneacetone)dipalladium, 9.5 mg of 4,5-bis(diphenylphosphino)-9,9-dimethylxanthene, followed by purification over a column charged with Deloxan® THP II and the further addition of n-butanol. At a reaction temperature of 80-110° C., the water formed is removed by azeotropic distillation. The product is purified by distillation at reduced pressure. Yield: 189 g (84% of theory) of butyl ethylphosphonite.

Example 3

Example 1 is repeated with 198 g of phosphinic acid, 198 g of water, 84 g of ethylene, 6.1 mg of palladium(II) sulfate, 25.8 mg of 9,9-dimethyl-4,5-bis(diphenylphosphino)-2,7-sulfonatoxanthene disodium salt, followed by purification over a column charged with Deloxan® THP II and the further addition of n-butanol. At a reaction temperature of 80-110° C., the water formed is removed by azeotropic distillation. The product is purified by distillation at reduced pressure. Yield: 374 g (83% of theory) of butyl ethylphosphonite.

Example 4

A 500 ml five-neck flask equipped with gas inlet tube, thermometer, high-performance stirrer and reflux condenser with gas incineration is charged with 94 g (1 mol) of ethylphosphonous acid (produced as in Example 1). Ethylene oxide is introduced at room temperature. A reaction temperature of 70° C. is set with cooling, followed by further reaction at 80° C. for one hour. The ethylene oxide takeup is 65.7 g. The acid number of the product is less than 1 mg KOH/g. Yield: 129 g (94% of theory) of 2-hydroxyethyl ethylphosphonite as colorless, water-clear product.

Example 5

564 g (6 mol) of ethylphosphonous acid (produced as in Example 1) are dissolved in 860 g of water and initially charged to a 5 l five-necked flask equipped with thermometer, reflux condenser, high-performance stirrer and dropping funnel. After heating the reaction mixture to 100° C., 371 g (7 mol) of acrylonitrile and 500 g of a 5% strength sodium peroxodisulfate solution (1.5 mol % based on acrylonitrile) are added dropwise at atmospheric pressure over 1 h. The water is then distilled off in vacuo. The residue is taken up in tetrahydrofuran and extracted. The insoluble salts are filtered off. The solvent of the filtrate is removed in vacuo and the residue is recrystallized from acetone to leave 732 g (83% of theory) of ethyl-(2-cyanoethyl)phosphinic acid as oil.

Example 6

94 g (1 mol) of ethylphosphonous acid (produced as in Example 1) and 67 g (1 mol) of methacrylonitrile are introduced into a four-neck round-bottom flask equipped with stirrer, reflux condenser, thermometer and nitrogen inlet and heated. At about 100° C., 98.4 g of a 5% strength solution of AIBN in ethanol are added dropwise over 1 h. Thereafter, the solvent was distilled off in vacuo to leave 137 g of ethyl(2-cyano-2-methylethyl)phosphinic acid.

Example 7

A 1 l five-neck flask equipped with thermometer, reflux condenser, high-performance stirrer and dropping funnel was charged with 447 g (3 mol) of butyl ethylphosphonite (produced as in Example 3) and 159 g (3 mol) of acrylonitrile. While stirring, 15 ml of sodium butoxide (30% strength in butanol) are added dropwise at a rate such that a reaction temperature of max. 120° C. becomes established. The crude product thus obtained is distilled in vacuo to obtain 554 g (91% of theory) of butyl ethyl(2-cyanoethyl)phosphinate as colorless liquid.

Example 8

A 1 L capacity loop reactor is filled with a mixture of 914 g (4.5 mol) of butyl ethyl(2-cyanoethyl)phosphinate (produced as in Example 7) and 62 g (1.35 mol) of ethanol. After starting the pump, a mixture of 726 g (6.00 mol) of ethyl ethylphosphonite and 318 g (6.00 mol) of acrylonitrile and also a solution of 22.4 g (0.20 mol) of potassium butoxide in 193 g (2.61 mol) of butanol are metered in per hour, while a cooling water circuit is used to maintain a temperature of about 40° C. The overflowing crude product is collected for 30 hours and together with the product discharged from the reactor gave a total amount of 37.1 kg. After removal of low boilers by distillation under water jet vacuum and filtration, the product was vacuum distilled in a thin-film evaporator to obtain 29.1 kg (143.5 mol) of butyl ethyl(2-cyanoethyl)phosphinate. Minus the amount initially charged to the reactor this corresponds to a phosphorus yield of 93.0% at a rate of about 970 g/l*h. As this example shows, continuous production of the monocyano-functionalized dialkylphosphinic esters in good space-time yields is possible.

Example 9

150 g (1 mol) of the butyl ethylphosphonite (produced as in Example 2) and 80 g (1.2 mol) of methacrylonitrile in 217 g of toluene are heated to about 100° C. While stirring, 124 g of a 10% strength solution of Wako V65 in toluene are metered in. The solvent is distilled off in vacuo to obtain 182 g (84% of theory) of butyl ethyl(2-cyano-2-methylethyl)phosphinate.

Example 10

441 g (3 mol) of the ethyl(2-cyanoethyl)phosphinic acid obtained (produced as in Example 5) are at 85° C. dissolved in 400 ml of toluene and admixed with 888 g (12 mol) of butanol. At a reaction temperature of about 100° C., the water formed is removed by azeotropic distillation. The product butyl ethyl(2-cyanoethyl)-phosphinate is purified by distillation at reduced pressure.

Example 11

540 g (3.0 mol) of ethyl(2-cyano-2-methylethyl)phosphinic acid (produced as in Example 6) are at 80° C. dissolved in 400 ml of toluene and admixed with 315 g (3.5 mol) of 1,4-butanediol and esterified at about 100° C. during 4 h in a distillation apparatus equipped with a water trap. After the esterification has ended, the toluene is separated off in vacuo to leave 643 g (92% of theory) of 4-hydroxybutyl ethyl(2-cyano-2-methylethyl)phosphinate as colorless oil.

Example 12

441 g (3.0 mol) of ethyl(2-cyanoethyl)phosphinic acid (produced as in Example 5) are at 85° C. dissolved in 400 ml of toluene and admixed with 248 g (4 mol) of ethylene glycol and esterified at about 100° C. in a distillation apparatus equipped with water trap during 4 h. On completion of the esterification the toluene and excess ethyl glycol is removed in vacuo to leave 510 g (89% of theory) of 2-hydroxyethyl ethyl(2-cyanoethyl)phosphinate as colorless oil.

Example 13

In a stirred apparatus, 147 g (1 mol) of ethyl(2-cyanoethyl) phosphinic acid (produced as in Example 5) are dissolved in 200 ml (2 mol) of concentrated hydrochloric acid. The efficiently stirred mixture was heated to about 90° C. and reacted at that temperature for about 6 hours. The reaction solution is cooled down, and ammonium hydrochloride formed is filtered off. Concentrating the reaction solution results in further precipitation of ammonium hydrochloride, which is removed by filtering the hot reaction solution. The water is then completely distilled off in vacuo. The residue is taken up in acetic acid and extracted. The insoluble salts are filtered off. The solvent of the filtrate is removed in vacuo and the residue is recrystallized from acetone to obtain 161 g (97% of theory) of 3-(ethylhydroxyphosphinyl)propionic acid as a solid material.

Example 14

In a stirred apparatus, 217 g (1 mol) of butyl ethyl(2-methyl-2-cyano-ethyl)phosphinate (produced as in Example 9) are dissolved in 200 ml (2 mol) of concentrated hydrochloric acid. The efficiently stirred mixture was heated to about 90° C. and reacted at that temperature for about 8 hours. The reaction solution is cooled down, and ammonium hydrochloride formed is filtered off. Concentrating the reaction solution results in further precipitation of ammonium hydrochloride, which is removed by filtering the hot reaction solution. The water is then completely distilled off in vacuo. The residue is taken up in acetic acid and extracted. The insoluble salts are filtered off. The solvent of the filtrate is removed in vacuo and the residue is recrystallized from acetone to obtain 169 g (94% of theory) of 3-(ethylhydroxyphosphinyl)-2-methyl-propionic acid as a solid material.

Example 15

A stirred apparatus is initially charged with 150 g of butanol, 65 g of water, 150 g (3.75 mol) of sodium hydroxide and 183 g (1.25 mol) of ethyl(2-cyanoethyl)-phosphinic acid (produced as in Example 5). The efficiently stirred mixture was heated to about 120° C. and reacted at that temperature for about 6 hours. Then, 250 ml of water were added and the butanol was removed from the reaction mixture by distillation. Following the addition of a further 500 ml of water, the mixture is neutralized by addition of about 184 g (1.88 mol) of concentrated sulfuric acid. The water is then distilled off in vacuo. The residue is taken up in tetrahydrofuran and extracted. The insoluble salts are filtered off. The solvent of the filtrate is removed in vacuo and the residue is recrystallized from acetone to obtain 203 g (98% of theory) of 3-(ethylhydroxyphosphinyl)propionic acid as a solid material.

Example 16

A stirred apparatus is initially charged with 150 g of ethanol, 65 g of water, 150 g (3.75 mol) of sodium hydroxide and 183 g (1.25 mol) of ethyl(2-cyanoethyl)-phosphinic acid (produced as in Example 5). The mixture was heated under reflux and reacted at that temperature for about 10 hours. Then water and the butanol were removed from the reaction mixture by distillation. Following the addition of a further 500 ml of water, the mixture was neutralized by addition of about 61 g (0.63 mol) of concentrated sulfuric acid. The water is then distilled off in vacuo. The residue is taken up in ethanol and the insoluble salts are filtered off. The solvent of the filtrate is removed in vacuo to obtain 234 g (89% of theory) of 3-(ethylhydroxyphosphinyl)propionic acid sodium salt as a solid material.

Example 17

A stirred apparatus is initially charged with 150 g of butanol, 65 g of water, 150 g (3.75 mol) of sodium hydroxide and 271 g (1.25 mol) of butyl ethyl(2-cyano-2-methylethyl)phosphinate (produced as in Example 9). The efficiently stirred mixture was heated to about 120° C. and reacted at that temperature for about 8 hours. Then, 250 ml of water were added and the butanol was removed from the reaction mixture by distillation. Following the addition of a further 500 ml of water, the mixture was neutralized by addition of about 184 g (1.88 mol) of concentrated sulfuric acid. The water is then distilled off in vacuo. The residue is taken up in tetrahydrofuran and extracted. The insoluble salts are filtered off. The solvent of the filtrate is removed in vacuo and the residue is recrystallized from acetone to obtain 216 g (96% of theory) of 3-(ethylhydroxyphosphinyl)-2-methylpropionic acid as a solid material.

Example 18

498 g (3 mol) of 3-(ethylhydroxyphosphinyl)propionic acid (produced as in Example 15) are dissolved in 860 g of water and initially charged into a 5 l five-neck flask equipped with thermometer, reflux condenser, high-performance stirrer and dropping funnel and neutralized with about 480 g (6 mol) of 50% sodium hydroxide solution. The water is subsequently distilled off in vacuo to leave 624 g (99% of theory) of 3-(ethylhydroxyphosphinyl)propionic acid sodium salt as a solid material.

Example 19

630 g (3 mol) of 3-(ethylhydroxyphosphinyl)propionic acid sodium salt (produced as in Example 16) are dissolved in 860 g of water and initially charged into a 5 l five-neck flask equipped with thermometer, reflux condenser, high-performance stirrer and dropping funnel and neutralized by addition of about 147 g (1.5 mol) of concentrated sulfuric acid. The water is subsequently distilled off in vacuo. The residue is taken up in ethanol and the insoluble salts are filtered off. The solvent of the filtrate is removed in vacuo to leave 488 g (98% of theory) of 3-(ethylhydroxy-phosphinyl)propionic acid as a solid material.

Example 20

498 g (3 mol) of the 3-(ethylhydroxyphosphinyl)propionic acid obtained (produced as in Example 15) are at 85° C. dissolved in 400 ml of toluene and admixed with 888 g (12 mol) of butanol. At a reaction temperature of about 100° C., the water formed is removed by azeotropic distillation. The butyl 3-(ethylbutoxyphosphinyl)propionate product is purified by distillation at reduced pressure.

Example 21

540 g (3.0 mol) of 3-(ethylhydroxyphosphinyl)-2-methyl-propionic acid (produced as in Example 17) are at 80° C. dissolved in 400 ml of toluene and admixed with 594 g (6.6 mol) of 1,4-butanediol and esterified at about 100° C. in a distillation apparatus equipped with water trap during 4 h. On completion of the esterification the toluene is removed in vacuo to leave 894 g (92% of theory) of 4-hydroxybutyl 3-(ethyl-4-hydroxybutoxyphosphinyl)-2-methylpropionate as colorless oil.

Example 22

To 276 g (2 mol) of butyl 3-(ethylbutoxyphosphinyl)propionate (produced as in Example 20) are added 155 g (2.5 mol) of ethylene glycol and 0.4 g of potassium titanyloxalate, followed by stirring at 200° C. for 2 h. Volatiles are distilled off by gradual evacuation to leave 244 g (98% of theory) of 2-hydroxyethyl 3-(ethyl-2-hydroxyethoxyphosphinyl)propionate.

Example 23

996 g (6 mol) of 3-(ethylhydroxyphosphinyl)propionic acid (produced as in Example 15) are dissolved in 860 g of water and initially charged into a 5 l five-neck flask equipped with thermometer, reflux condenser, high-performance stirrer and dropping funnel and neutralized with about 960 g (12 mol) of 50% sodium hydroxide solution. A mixture of 2583 g of a 46% aqueous solution of $Al_2(SO_4)_3 \cdot 14\ H_2O$ is added at 85° C. The solid material obtained is subsequently filtered off, washed with hot water and dried at 130° C. in vacuo. Yield: 1026 g (94% of theory) of 3-(ethylhydroxyphosphinyl)propionic acid aluminum(III) salt as colorless salt.

Example 24

180 g (1 mol) of 3-(ethylhydroxyphosphinyl)-2-methylpropionic acid (produced as in Example 17) and 170 g of titanium tetrabutoxide are refluxed in 500 ml of toluene for 40 hours. The resulting butanol is distilled off from time to time with proportions of toluene. The solution formed is subsequently freed of solvent to leave 184 g (91% of theory) of 3-(ethylhydroxyphosphinyl)-2-methylpropionic acid titanium salt.

Example 25

To 25.4 g of 2-hydroxyethyl 3-(ethyl-2-hydroxyethoxyphosphinyl)propionate (produced as in Example 22) are added 290 g of terephthalic acid, 188 g of ethylene glycol and 0.34 g of zinc acetate, and the mixture is heated to 200° C. for 2 h. Then, 0.29 g of trisodium phosphate anhydrate and 0.14 g of antimony(III) oxide are added, followed by heating to 280° C. and subsequent evacuation.

The melt obtained (357 g, phosphorus content 0.9%) is used to injection mold test specimens 1.6 mm in thickness for measurement of the limiting oxygen index (LOI) to ISO 4589-2 and also for the UL 94 (Underwriter Laboratories) flammability test. The test specimens thus produced gave an LOI of 42% $O_2$ and were UL 94 classified as flammability class V-0. Corresponding test specimens without 2-hydroxyethyl 3-(ethyl-2-hydroxyethoxyphosphinyl)propionate gave an LOI of just 31% $O_2$ and were UL 94 classified as flammability class V-2 only. The polyester molded article containing 2-hydroxyethyl 3-(ethyl-2-hydroxyethoxyphosphinyl)-propionate hence clearly has flame-retardant properties.

Example 26

To 15.2 g of 3-(ethylhydroxyphosphinyl)-2-methylpropionic acid (produced as in Example 17) are added to 12.9 g of 1,3-propylene glycol and at 160° C. the water formed by esterification is stripped off. Then, 378 g of dimethyl terephthalate, 152 g of 1,3-propanediol, 0.22 g of tetrabutyl titanate and 0.05 g of lithium acetate are added and the mixture is initially heated at 130 to 180° C. for 2 h with stirring and thereafter at 270° C. at underpressure. The polymer (438 g) contains 0.6% of phosphorus, the LOI is 34.

Example 27

To 14 g of 3-(ethylhydroxyphosphinyl)propionic acid (produced as in Example 13) are added 367 g of dimethyl terephthalate, 170 g of 1,4-butanediol, 0.22 g of tetrabutyl titanate and 0.05 g of lithium acetate and the mixture is initially heated at 130 to 180° C. for 2 h with stirring and thereafter at 270° C. at underpressure. The polymer (427 g) contains 0.6% of phosphorus, the LOI is 34, the LOI of untreated polybutylene terephthalate is 23.

Example 28

In a 250 ml five-neck flask equipped with reflux condenser, stirrer, thermometer and nitrogen inlet, 100 g of a bisphenol A bisglycidyl ether having an epoxy value of 0.55 mol/100 g (Beckopox EP 140, from Solutia) and 24.1 g (0.13 mol) of 3-(ethylhydroxyphosphinyl)-2-methylpropionic acid (produced as in Example 17) are heated to not more than 150° C. with stirring. A clear melt forms after 30 min. After a further hour of stirring at 150° C., the melt is cooled down and triturated to obtain 118.5 g of a white powder having a phosphorus content of 3.3% by weight.

Example 29

In a 2 l flask equipped with stirrer, water trap, thermometer, reflux condenser and nitrogen inlet, 29.4 g of phthalic anhydride, 19.6 g of maleic anhydride, 24.8 g of propylene glycol, 18.7 g of 2-hydroxyethyl 3-(ethyl-2-hydroxyethoxyphosphinyl)-propionate (produced as in Example 22), 20 g of xylene and 50 mg of hydroquinone are heated to 100° C. while stirring and with nitrogen being passed through. The heating operation is stopped when the exothermic reaction is started. After the reaction has died down, stirring is continued at about 190° C. After 14 g of water have been separated off, the xylene is distilled off and the polymer melt is cooled down. This gives 91.5 g of a white powder having a phosphorus content of 2.3% by weight.

Example 30

A mixture of 50% by weight of polybutylene terephthalate, 20% by weight of 3-(ethylhydroxyphosphinyl)propionic acid aluminium(III) salt (produced as in Example 23) and 30% by weight of glass fibers are compounded on a twin-screw extruder (Leistritz LSM 30/34) at temperatures of 230 to 260° C. to form a polymeric molding material. The homogenized polymeric strand was hauled off, water bath cooled and then pelletized. After drying, the molding materials are processed on an injection molding machine (Aarburg Allrounder) at 240 to 270° C. to form polymeric molded articles which achieved a UL-94 classification of V-0.

Example 31

A mixture of 53% by weight of nylon-6,6, 30% by weight of glass fibers, 17% by weight of 3-3-(ethylhydroxyphosphinyl)-2-methylpropionic acid titanium salt (produced as in Example 24) are compounded on a twin-screw extruder (Leistritz LSM 30/34) to form polymeric molding materials. The homogenized polymeric strand was hauled off, water bath cooled and then pelletized. After drying, the molding materials are processed on an injection molding machine (Aarburg Allrounder) at 260 to 290° C. to form polymeric molded articles which achieved a UL-94 classification of V-0.

What is claimed is:
1. A method for producing monocarboxy-functionalized dialkylphosphinic acids, esters or salts, comprising the steps of:
a) reacting a phosphinic acid source (I)

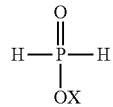

(I)

with one or more olefins (IV)

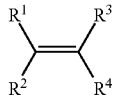

in the presence of a catalyst A to form an alkylphosphonous acid, salt or ester (II)

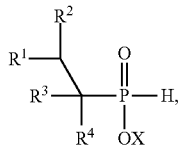

b) reacting the alkylphosphonous acid, salt or ester (II) with one or more acrylonitrile (V)

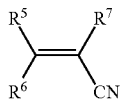

in the presence of a catalyst B to form a monofunctionalized dialkylphosphinic acid derivative (VI)

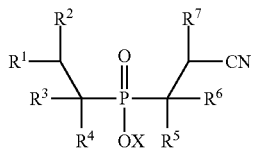

and c) reacting the monofunctionalized dialkylphosphinic acid derivative (VI) in the presence of a catalyst C to form a monocarboxy-functionalized dialkylphosphinic acid derivative (III)

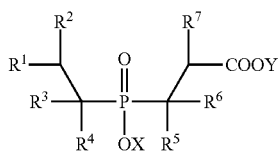

where $R^1$, $R^2$, $R^3$, $R^4$, $R^5$, $R^6$, $R^7$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, $(CH_2)_m$OH, $(CH_2)_m$NH$_2$, $(CH_2)_m$NCS, $(CH_2)_m$NC(S)NH$_2$, $(CH_2)_m$SH, $(CH_2)_m$S-2-thiazoline, $(CH_2)_m$SiMe$_3$, C(O)R$^8$, $(CH_2)_m$C(O)R$^8$, CH=CH-R$^8$ or CH=CH-C(O)R$^8$ and where R$^8$ is $C_1$-$C_8$-alkyl or $C_6$-$C_{18}$-aryl and m is an integer from 0 to 10 and X and Y are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, $(CH_2)_k$OH, CH$_2$—CHOH—CH$_2$OH, $(CH_2)_k$O(CH$_2)_k$H, $(CH_2)_k$—CH(OH)—$(CH_2)_k$H, $(CH_2$—CH$_2$O)$_k$H, $(CH_2$—C[CH$_3$]HO)$_k$H, $(CH_2$—C[CH$_3$]HO)$_k$(CH$_2$—CH$_2$O)$_k$H, $(CH_2$—CH$_2$O)$_k$(CH$_2$—C[CH$_3$]HO)H, $(CH_2$—CH$_2$O)$_k$-alkyl, $(CH_2$—C[CH$_3$]HO)$_k$-alkyl, $(CH_2$—C[CH$_3$]HO)$_k$(CH$_2$—CH$_2$O)$_k$-alkyl, $(CH_2$—CH$_2$O)$_k$(CH$_2$—C[CH$_3$]HO)O-alkyl, $(CH_2)_k$—CH=CH$(CH_2)_k$H, $(CH_2)_k$NH$_2$ or $(CH_2)_k$N[$(CH_2)_k$H]$_2$, where k is an integer from 0 to 10, Mg, Ca, Al, Sb, Sn, Ge, Ti, Fe, Zr, Zn, Ce, Bi, Sr, Mn, Cu, Ni, Li, Na, K, H, a protonated nitrogen base or a combination thereof and the catalyst A is selected from the group of transition metals, transition metal compounds, catalyst systems composed of a transition metal or transition metal compound and at least one ligand and a combination thereof, and the catalyst B is selected from the group consisting of peroxide-forming compounds, peroxo compounds, azo compounds, comprises alkali hydrides, alkaline earth metal hydrides, alkali alkoxides, alkaline earth metal alkoxides and a combination thereof and the catalyst C is an acid or a base.

2. The method according to claim 1 wherein the monocarboxy-functionalized dialkylphosphinic acid, its salt or ester III obtained after step c) is reacted in a step d) with metal compounds of Mg, Ca, Al, Sb, Sn, Ge, Ti, Fe, Zr, Zn, Ce, Bi, Sr, Mn, Li, Na, K, a protonated nitrogen base or a combination thereof to form the monocarboxy-functionalized dialkylphosphinic acid salts III of these metals, of a nitrogen compound or a combination thereof.

3. The method according to claim 1, wherein the alkylphosphonous acid, salt or ester (II) obtained after step a), the monofunctionalized dialkylphosphinic acid, salt or ester (VI) obtained after step b), the monocarboxy-functionalized dialkylphosphinic acid, salt or ester (III) obtained after step c), the reaction solution thereof or a combination thereof are esterified with an alkylene oxide or an alcohol M-OH, M'-OH, and the alkylphosphonous ester (II), monofunctionalized dialkylphosphinic ester (VI) monocarboxy-functionalized dialkylphosphinic ester (III) or combination thereof is subjected to the reaction steps b) or c).

4. The method according to claim 1, wherein the groups $C_6$-$C_{18}$-aryl, $C_6$-$C_{18}$-aralkyl and $C_6$-$C_{18}$-alkylaryl are substituted with SO$_3$X$_2$, —C(O)CH$_3$, OH, CH$_2$OH, CH$_3$SO$_3$X$_2$, PO$_3$X$_2$, NH$_2$, NO$_2$, OCH$_3$, SH, OC(O)CH$_3$ or a combination thereof.

5. The method according to claim 1, wherein $R^1$, $R^2$, $R^3$, $R^4$, $R^5$, $R^6$, $R^7$ are identical or different and are each independently H, methyl, ethyl, n-propyl, isopropyl, n-butyl, isobutyl, tert-butyl phenyl or a combination thereof.

6. The method according to claim 1, wherein X and Y are identical or different and are each H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl, glycerol or a combination thereof.

7. The method according to claim 1, wherein the transition metals, transition metal compounds or a combination thereof are from the seventh and eighth transition groups.

8. The method according to claim 1, wherein the transition metals transition metal compounds or combination thereof are rhodium, nickel, palladium, platinium or ruthenium.

9. The method according to claim 1, wherein the catalyst B is hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-t-butyl peroxide and/or peroxodisulfuric acid, azobisisobutyronitrile, 2,2'-azobis(2-amidinepropane) dihydrochloride, 2,2'-azobis(N,N'-dimethyleneisobutyramidine) dihydrochloride, lithium, lithium hydride, lithium aluminohydride, methyllithium, butyllithium, t-butyllithium, lithium diisopropylamide, sodium, sodium hydride, sodium borohydride, sodium methoxide, sodium ethoxide, sodium butoxide, potassium methoxide, potassium ethoxide, potassium butoxide or a combination thereof.

10. The method according to claim 1, wherein the catalyst C is selected from the group consisting of metals, metal hydrides, metal hydroxides, metal alkoxides and mineral acids.

11. The method according to claim 1, wherein the one or more acrylonitriles (V) areacrylonitrile, methacrylonitrile, ethyl 2-cyanoacrylate, 3-phenylacrylonitrile or 2-methyl-2-butenenitrile.

12. The method according to claim 1, wherein the alcohol of the general formula M-OH is a linear or branched, saturated or unsaturated, monohydric organic alcohol having a carbon chain length of $C_1$-$C_{18}$ and the alcohol of the general formula M'-OH is a linear or branched, saturated or unsaturated polyhydric organic alcohol having a carbon chain length of $C_1$-$C_{18}$.

* * * * *